US00PP31314P2

(12) United States Plant Patent
Hansen

(10) Patent No.: US PP31,314 P2
(45) Date of Patent: Dec. 31, 2019

(54) ***SEDUM* PLANT NAMED 'STEEL THE SHOW'**

(50) Latin Name: ***Sedum* hybrid**
Varietal Denomination: Steel the Show

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,948

(22) Filed: Feb. 4, 2019

(51) Int. Cl.
*A01H 5/00* (2018.01)
*A01H 6/32* (2018.01)

(52) U.S. Cl.
USPC ..... Plt./479
CPC ..... *A01H 6/32* (2018.05)

(58) Field of Classification Search
USPC ..... Plt./479
CPC ..... A01H 5/00
See application file for complete search history.

*Primary Examiner* — Kent L Bell

(57) ABSTRACT

The new and distinct cultivar of perennial *Sedum* plant named 'Steel the Show' is characterized by drought-tolerant, winter-hardy, dense, low, compact mounds of silvery blue-green foliage. The flowers open much later than most *Sedum* producing a rich, rosy-pink effect for about four weeks beginning in early fall. The new plant stays tightly compact and resists opening in the center later in the season. The new plant is useful for landscaping as a specimen plant, en masse or in a container.

1 Drawing Sheet

Botanical designation: *Sedum* hybrid.
Cultivar denomination: 'Steel the Show'.

STATEMENT REGARDING PRIOR DISCLOSURES UNDER 37 CFR 1.77(B)(6)

The non-enabling disclosure of the claimed plant, in the form of a photograph and brief description on a website operated by Walters Gardens, Inc. on Feb. 1, 2018. The claimed plant was first sold on Jul. 9, 2018 by Walters Gardens, Inc., who obtained the plant and all information relating thereto, from the inventor. No plants of *Sedum* 'Steel the Show' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Sedum* or Stonecrop plant, botanically known as *Sedum* and hereinafter referred to by the cultivar name 'Steel the Show'. There are over 300 recognized species of the genus *Sedum*.

The new plant is an insect pollination controlled by the inventor between a select unnamed plant of *Sedum cauticola* (not patented) as the female parent and 'Mongolian Stardust' (not patented) as the male parent on Sep. 1, 2012 in a research facility at a wholesale perennial nursery in Zeeland, Mich. The new plant was initially selected in the autumn of 2014 and assigned the breeder code 12-25-4 for the remainder of the trial period. 'Steel the Show' was approved for final evaluation in the fall of 2015. Initial propagation was by basal shoot cuttings since the January of 2016 at a wholesale perennial nursery in Zeeland, Mich. has shown that the unique features of this new *Sedum* plant are stable and reproduced true to type in successive generations.

SUMMARY OF THE INVENTION

Plants of *Sedum* 'Steel the Show' have not been observed under all possible environmental conditions. The phenotype may vary somewhat with variations in environment such as temperature, available water, fertility and light intensity without, however, any variation in genotype.

The closest comparison varieties known to the inventor include: 'Pure Joy' U.S. Plant Pat. No. 24,194, 'Superstar' U.S. Plant patent application Ser. No. 15/932,171, and 'Dazzleberry' U.S. Plant Pat. No. 22,457. 'Pure Joy' has a larger and taller habit and the flowers are a lighter pink. 'Superstar' has a slightly larger and taller habit, the flower color is more intense rosy-pink with hot pink carpels and the foliage has a smoky gray overlay. 'Dazzleberry' has a smoky gray foliage overlay and the flowers are vibrant raspberry-colored. 'Mongolian Stardust' has blue-green foliage, more open habit, and the flowers are near white. The *Sedum cauticola* parent has blue-gray foliage, pink flowers with carpels that age to carmine-red, and the habit is much shorter.

The following traits have been repeatedly observed and are determined to be the unique characteristics of *Sedum* 'Steel the Show'. The following characteristics in combination distinguish 'Steel the Show' as a new and distinct Stonecrop plant unique from all other Stonecrop plants known to the inventor:

1. Short and compact plant habit.
2. Plants are drought tolerant and winter hardy to at least USDA zone 3.
3. Small leaves of silvery, gray-green.
4. Stems and foliage stay tightly compact resistant to open in center of plant.
5. Late blooming with flowers of rich, rosy pink.

BRIEF DESCRIPTION OF THE PHOTOGRAPH

The photograph of the new plant demonstrates the unique traits and the overall appearance of *Sedum* 'Steel the Show'. The colors are as accurate as reasonably possible with color reproductions of this type. Variations in ambient light spectrum, source and direction may cause the appearance of minor variation in color. The plants used in the photographs were three-year-old plants grown in an open, full-sun display garden at a wholesale perennial nursery in Zeeland, Mich. with supplemental water and fertilizer when needed. No plant growth regulators have been used.

DETAILED BOTANICAL DESCRIPTION

Figure 1:
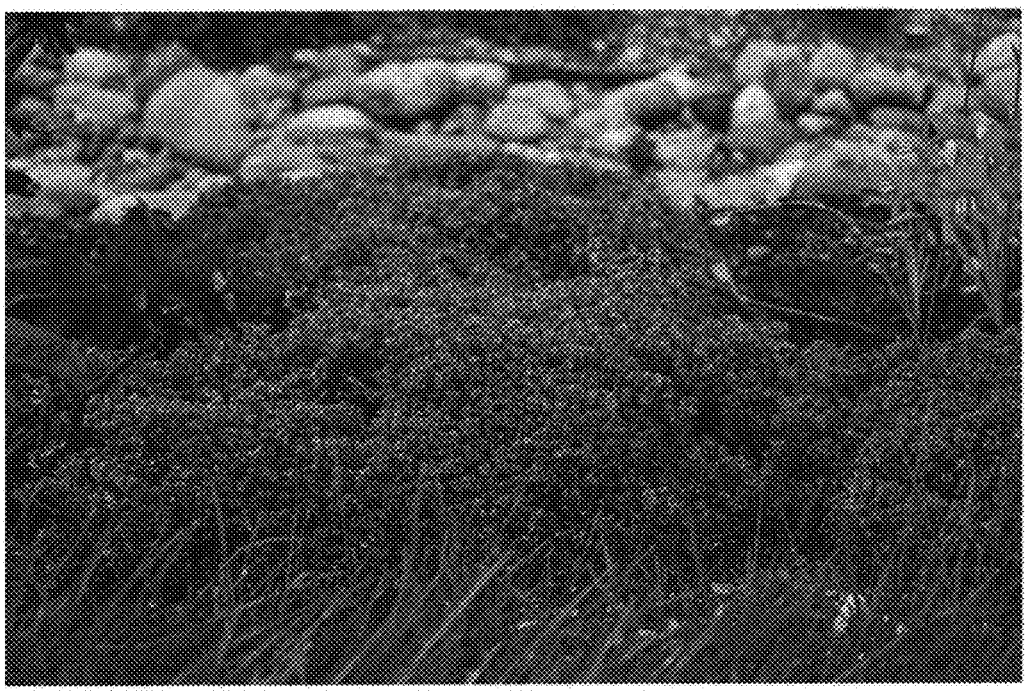
FIG. 1 shows the plant in full flower habit.
Figure 2:
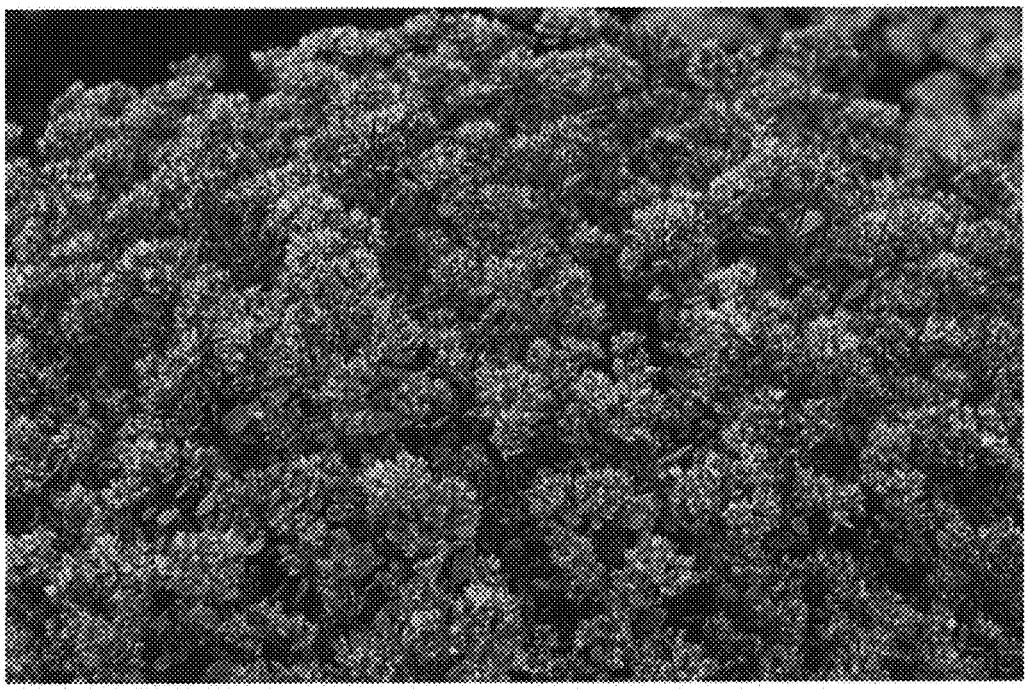
FIG. 2 shows a close-up of the plant in early flowering with foliage and buds.

The following is a detailed description of three-year-old plants of the new cultivar as grown outdoors in a full sun trial plot and also as greenhouse grown specimens at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Botanical designation: *Sedum* hybrid;

Cultivar denomination: 'Steel the Show';

Parentage: Select unnamed plant of *Sedum cauticola* as the female or seed parent; 'Mongolian Stardust' as the male or pollen parent;

Asexual propagation: Stem cuttings and division;

Time to initiate roots: About two weeks;

Time to finish a 3.7 liter flowering container: About three months in the summer from a rooted 2.5 cm plug;

Root description: Thick, fleshy; freely branching; creamy white to light tan in color; color nearest RHS 158D depending on soil content;

Plant habit: Winter-hardy, succulent, herbaceous perennial; low mounded; multiple stiff stems, upright to outright, arising from a dense base; flower heads freely branching; dense and full, resists developing an open center later in the season;

Growth rate: Moderately vigorous;

Plant size: About 20.0 cm tall and 56.0 cm wide in full flower;

Main stems: Glabrous; about 350 per plant; diameter at stem base about 3.0 mm, average about 7.0 mm; about 18.0 cm long from base to initial flower cymes; maintaining foliage to base of stem; internodes average about 11.0 mm;

Main stem color: Variable; between nearest RHS 146B at base and in low light exposure and nearest RHS 183A in high light exposure;

Lateral branches: Glaucous; to about 4.0 cm long and 2.5 mm diameter;

Lateral branch color: Same as main stem;

Foliage: Opposite, simple; obovate to rhombic; smooth; glaucous and glabrous abaxial and adaxial; abaxial and adaxial surface matte; base cuneate; apex rounded and serrate with five teeth; thick, fleshy and succulent; to about 32.0 mm long, about 18.0 mm across near apex, and about 4.0 mm thick, average about 26.0 mm long, about 8.0 mm wide, about 3.5 mm thick; decreasing in size distally;

Foliage color: Developing leaves — adaxial and abaxial surface between RHS 122B and RHS 189B; late season nearest RHS N138C adaxial and abaxial;

Venation: Pinnate; color same as surrounding leaf tissue on both surfaces;

Flower: Rotate; upright; perfect; actinomophic; in terminal compound cymes; freely flowering habit with up to 500 per branched stem and 10,000 to 20,000 per plant, covering the entire foliage;

Flower size: About 10.0 mm across and 6.0 mm tall;

Flower facing: Upward to outwardly;

Flower fragrance: Not detected;

Flowering season: Beginning early fall, after most other *Sedum*, and continuing for about four weeks in Zeeland, Mich.;

Longevity: Individual flower remain effective for about four to six days on the plant; individual flowers persistent;

Flower buds about one day prior to opening: Narrow conic; apex acute; base rounded; about 4.0 mm long and 2.0 mm across;

Flower bud color: Exposed petals longitudinal center nearest RHS 63B; calyx nearest RHS N155B;

Inflorescence: To about 20.0 cm tall from first branch and 7.0 cm across;

Petals: Typically five; lanceolate; narrowly acute apex, base truncate, margin entire, glabrous; typically about 4.0 mm long and about 2.0 mm across;

Petal color: Adaxial base nearest RHS 63C, abaxial nearest RHS 62D;

Calyx: Rotate; 3.0 mm across and 1.5 mm long;

Sepals: Typically five; lanceolate; entire; glabrous and glaucous abaxial and adaxial; narrowly acute apex, truncate fused base; about 1.5 mm long and about 0.5 mm wide at fused base;

Sepal color: Nearest RHS 138D both adaxial and abaxial surfaces;

Peduncles: Glabrous; cylindrical; strong and stiff, yet flexible; freely branching, compound branches to 9.0 cm long; angle erect in center to nearly 60 degrees from perpendicular for branched portions; flowering portion about 11.5 cm long and 12.0 cm across;

Peduncle color: Nearest RHS 183A;

Pedicels: Cylindrical; glabrous; glaucous to lustrous; strong and stiff, yet flexible; to about 4.0 mm long and 0.7 mm diameter; average about 1.5 mm long and 0.7 mm diameter;

Pedicel color: Blend of RHS 177D, RHS 182D and RHS 146D;

Androecium: Stamens: typically five; to 5.0 mm long;

*Filaments*.—Thin; terete; upright; fused to petal base; about 4.5 mm long and about 0.5 mm diameter; color nearest RHS N155B.

*Anthers*.—Ellipsoidal; basifixed; about 0.5 mm long and about 0.3 mm wide; color nearest RHS 158B.

*Pollen*.—Not observed; sterile.

Gynoecium: Typically five, rarely four; cylindrical, conic in distal one third; to 4.5 mm long;

*Style*.—About 4.0 mm long and 1.5 mm diameter near middle; glabrous; color nearest RHS 63D, maturing to between RHS 61C and RHS 61B.

*Stigma*.—Minute; color nearest N155B.

*Ovary*.—Nearly cylindrical, tapering at apex to style; about 3.5 mm long and 1.5 mm diameter at base; color nearest N155B.

Seed and fruit: sterile;

Disease and pest resistance: Plants of the new *Sedum* 'Steel the Show' grow best with good drainage, full sun and moderate to low fertility. 'Steel the Show' is cold hardy from USDA zones 3 to 9. 'Steel the Show' tolerates heavy rains and wind and does not tend to develop an open center later in the season as many other stonecrop cultivars do. Other pest and disease resistance, tolerance and susceptibility outside that normal for Stonecrop is not known.

It is claimed:

1. The new and distinct perennial *Sedum* plant named 'Steel the Show' as herein described and illustrated.

* * * * *